United States Patent [19]

Yawata

[11] Patent Number: 5,054,647
[45] Date of Patent: Oct. 8, 1991

[54] ASEPTIC ORTHODONTIC DISPENSER

[75] Inventor: Haruyasu Yawata, Huntington Beach, Calif.

[73] Assignee: Ormco Corporation, Glendora, Calif.

[21] Appl. No.: 317,731

[22] Filed: Mar. 2, 1989

[51] Int. Cl.⁵ .............................................. B65H 3/00
[52] U.S. Cl. ....................................... 221/41; 221/55; 221/59; 221/63; 206/63.5
[58] Field of Search .................. 221/36, 41, 55–56, 221/59, 63, 226, 279, 303, 306, 309, 312 R, 312 C, 281, 307, 310, 33, 61, 62; 433/11, 18; 206/338–339, 303, 63.5, 63.3

[56] References Cited

U.S. PATENT DOCUMENTS

| | | | |
|---|---|---|---|
| 1,974,332 | 9/1934 | Hauck | 222/281 |
| 2,289,642 | 7/1942 | Flood | 242/55.2 |
| 2,294,001 | 8/1942 | Ritter | 221/279 X |
| 2,443,861 | 6/1948 | Johnston | 221/279 |
| 2,540,499 | 2/1951 | Towne | 222/281 |
| 2,601,852 | 7/1952 | Wendt | 221/279 X |
| 2,766,763 | 10/1956 | Shough | 222/281 X |
| 2,838,204 | 6/1958 | Snyder | 221/307 |
| 2,893,599 | 7/1959 | Kay | 221/281 X |
| 2,918,167 | 12/1959 | Lowen | 221/303 X |
| 3,018,921 | 1/1962 | Hermanson | 221/281 |
| 3,042,257 | 7/1962 | Dailey | 221/306 X |
| 3,193,094 | 7/1965 | Schulstad | 206/63.5 |
| 3,269,597 | 8/1966 | Passavanti | 221/281 X |
| 3,362,583 | 1/1968 | Showalter | 221/281 X |
| 3,412,897 | 11/1968 | Scater | 221/310 X |
| 3,976,219 | 8/1976 | Pagnoni | 221/310 |
| 4,038,753 | 8/1977 | Klein | 32/14 E |
| 4,071,948 | 2/1978 | Deutzmann | 221/310 X |
| 4,106,374 | 8/1978 | Dragan | 81/302 |
| 4,172,523 | 10/1979 | Weglage | 221/307 X |
| 4,217,686 | 8/1980 | Dragan | 29/413 |
| 4,330,271 | 5/1982 | Anderson | 433/3 |
| 4,502,612 | 3/1985 | Morrison | 221/307 X |
| 4,564,125 | 1/1986 | Esslinger | 221/306 X |
| 4,570,868 | 2/1986 | Wiggs et al. | 242/55.53 |
| 4,576,311 | 3/1986 | Horton et al. | 221/73 |
| 4,626,313 | 12/1986 | Karp | 156/362 |
| 4,874,348 | 10/1989 | Lafreniere et al. | 221/281 X |
| 4,901,847 | 2/1990 | Kesling | 206/63.5 |

FOREIGN PATENT DOCUMENTS 2060900  2/1972  Fed. Rep. of Germany ...... 221/307

Primary Examiner—Robert P. Olszewski
Assistant Examiner—Boris Milef
Attorney, Agent, or Firm—Marjama & Pincelli

[57] ABSTRACT

A dispenser for dispensing orthodontic O-rings comprises a main body portion having at least one storage and delivery chamber for holding a plurality of O-rings lying in a single plane and an outlet for allowing dispensing of O-rings. The main body is designed such that the O-rings are restrained from freely falling from the outlet. A further embodiment of the dispenser includes an ejection mechanism for assisting in the discharge of the O-rings.

24 Claims, 4 Drawing Sheets

ASEPTIC ORTHODONTIC DISPENSER

FIELD OF THE INVENTION

The present invention relates to devices for dispensing orthodontic appliances, and more specifically, for dispensing orthodontic O-rings.

BACKGROUND OF THE INVENTION

Orthodontic O-rings are used for securing orthodontic brackets to an orthodontic archwire. Because of their very small size, handling, storing and dispensing of orthodontic O-rings has been a problem. One suggested solution to this problem is illustrated by U.S. Pat. Nos. 4,217,686 and 4,038,753. In these patents, O-rings are provided on the runner on which they are molded. The O-rings are dispensed by pulling them off the runner. Since the supporting runner is made of the same material as the O-ring, the runner is quite flexible, therefore in order to be able to pull the O-rings off, a firm grip must be taken of the runner in the O-rings, usually by the use of the other hand. Additionally, if a tool of the type to be inserted in the center of the O-ring is used to remove the O-ring, the back of the O-ring dispenser must be reinforced to prevent bending back thereof. This is typically accomplished by placing a finger against the back side of the O-ring. As can be seen, the foregoing dispensing process significantly increases the risk of contamination of the O-rings yet to be dispensed. An additional problem with these type prior art dispensers is that a torn section is provided on the O-ring at the area where the O-ring is connected to the runner. This torn section may provide a weakening point for potential failure of the O-ring. This problem can be aggravated if the size of the connecting portion between the O-ring and runner is too large with respect to the size of the O-ring.

Applicants have invented an orthodontic O-ring dispensing device wherein the aseptic qualities of the appliance to be dispensed are maintained. The appliances are individually presented to allow a tool to grasp the outside of the O-ring or placed within the opening of the O-ring. The dispenser is simple in construction, is relatively low cost to manufacture and does not effect the strength of the orthodontic appliances to be dispensed.

SUMMARY OF THE INVENTION

In one aspect of the invention, there is provided a dispenser for dispensing orthodontic O-rings comprising a main body portion having at least one storage and delivery chamber for holding and dispensing a plurality of orthodontic O-rings and an outlet for allowing dispensing of O-rings. The main body further includes a means for restricting O-rings from freely falling from the outlet.

In another aspect of the present invention, there is provided a dispenser for dispensing a plurality of orthodontic O-rings comprising a main body portion having a base portion and a cover which are secured together so that the base portion can rotate within the cover. The base portion is provided with a plurality of recess portions, a shelf associated with each recess portion for supporting a single orthodontic O-ring, and an outlet for dispensing of the O-ring. The cover has an access opening capable of alignment with each of the recess portions to allow individual access to remove the O-ring.

DETAILED DESCRIPTION OF THE DRAWINGS

DETAILED DESCRIPTION OF THE INVENTION

Figure 1:
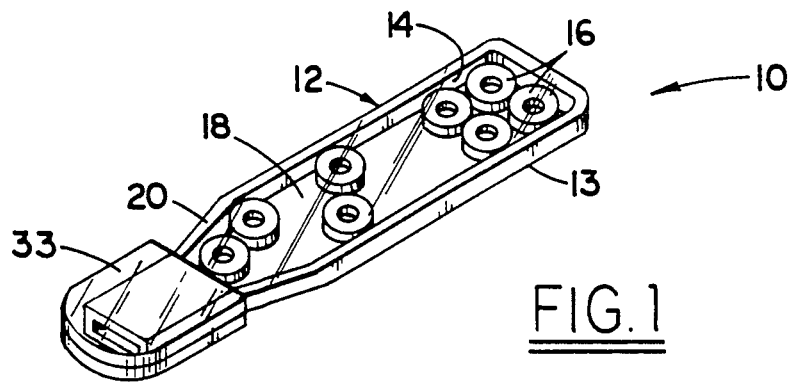
FIG. 1 is a perspective view of an orthodontic dispensive device made in accordance with the present invention.
Figure 2:
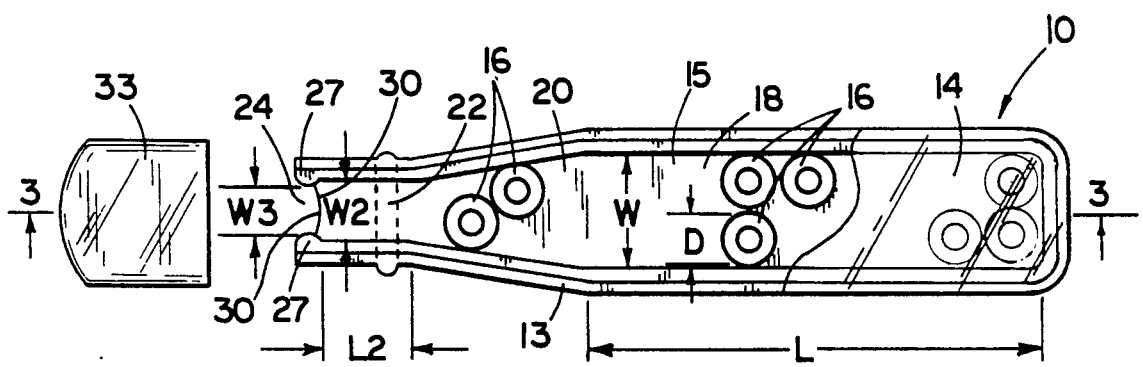
FIG. 2 is a top exploded plan view of the dispenser of FIG. 1.
Figure 3:
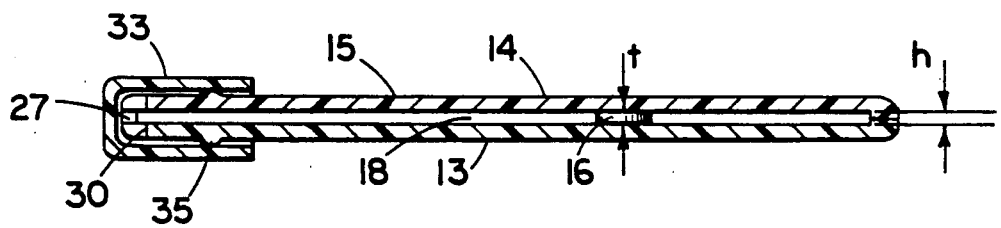
FIG. 3 is a side elevational view of the assembled dispenser of FIG. 1 as taken along the line III—III of FIG. 2.

In referring to FIGS. 1–3, there is illustrated dispensing device 10 made in accordance with the present invention. The device 10 comprises a main body portion 12 made of a plastic material, preferably of a transparent or translucent plastic. In the particular embodiment illustrated, the body 12 comprises a base section 13 and top cover 14 which are secured together. In the embodiment illustrated, base section 13 and top cover 14 snap together. The body portion includes a storage and delivery chamber 15, capable of holding a plurality orthodontic O-rings 16 typically available in the prior art. The chamber 15 is shaped such that the O-rings lie in a single plane. Therefore, chamber 15 has a substantially constant height H which is preferably slightly greater than the thickness T of O-rings 16 to be dispensed. In particular the embodiment illustrated, the orthodontic O-rings 16 are made of an elastic material, for example, a thermo-plastic polyurethane such as that sold by Dow Chemical under the trade name Pellathane 2363-80A, however, the O-rings may be made of any other suitable material so desired. The storage and delivery chamber 15 in the preferred embodiment illustrated includes a storage area 18, having a width W and length L. The storage and delivery chamber 15 further includes a funnel section 20 and a dispensing channel 22. The dispensing channel 22 has a substantially constant width W2 and a length L2. The width W2 preferably being only slightly greater than the diameter D of O- ring 16, but not too large such that only a single O-ring can be placed in a row. The funnel section 20 serves to gradually reduce the width W of storage area 18 to W2 so as to minimize the possibility of O-rings 16 jamming in device 10. Dispensing channel 22 terminates at an outlet 24 for dispensing of O-rings 16. The dispenser 10 is further provided with restricting means for restricting the dispensing of the O-rings 16 from outlet 24 to prevent O-rings 16 from simply falling out of dispensing channel 22. In the particular embodiment illustrated restricting means comprises a pair of projections 27 disposed at outlet 24 for restricting the width of outlet 24 to a width W3 which is designed to be slightly less than the diameter D of the orthodontic O-rings so that the O-ring 16 must be slightly deformed in order to pass through outlet 24. In this manner the O-rings 16 are prevented from simply falling out of dispensing channel 22. In the embodiment illustrated, restricting means comprises a pair of oppositely disposed projections that are preferably molded as part of the base section 13, however, the present invention is not so limited. If desired, only a single projection 27 may be provided on one side of outlet 24 and formed in any desired manner. All that is required is that means be provided to restrict O-rings from freely coming out of dispensing channel 22.

Figure 4A:
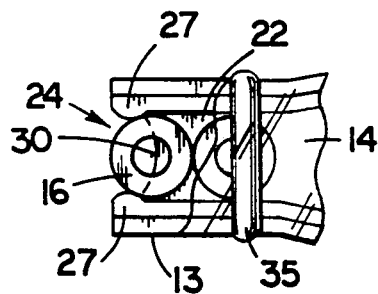
FIG. 4a is an enlarged fragmenting view of FIG. 2 of the area around outlet 24, illustrating how an O-ring is presented for dispensing.
Figure 4B:
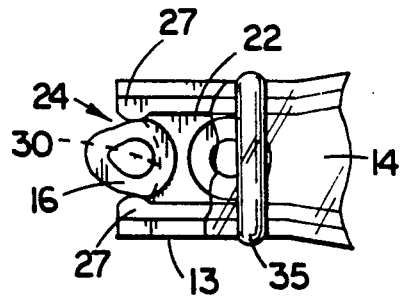
FIG. 4b is a view similar to FIG. 4a illustrating the deformation of the O-ring as it is being dispensed through the outlet.

The orthodontic dispenser 10 is further provided with a recess portion 30 in base and cover 14 at outlet 24 for allowing easy dispensing of the orthodontic O-ring 16 from the dispenser 10. The recess or cut away portion 30 is shaped such that when an O-ring 16 is disposed at the end of dispensing channel 22 adjacent projections 27 as illustrated in FIGS. 2 and 4a, a sufficient amount of O-ring 16 is exposed so as to allow easy access to both sides of the O-ring 16 to allow removal by a hemostat, or other similar like tool used to ligate orthodontic O-rings, or for the placement of a ligating tool within the opening 30 of orthodontic O-ring 16. The O-ring 16 is simply dispensed from dispenser 10 simply by pulling it through outlet 24 as shown in FIG. 4b.

A cap or cover 33 is provided for sealing outlet 24 from the environment. The cover 33 is held in place by a ridge formed on the outer surface of base section 13 and top cover 14, preferably cover 33 is made of the same material top cover and base section 13.

In order to more fully understand the present invention, a brief discription of its use will now be discussed. The body 12 is placed in an orthodontist's hand and is manipulated such that the O-rings 16 fill dispensing channel 22. A dispensing tool, such as a hemostat, is placed about the O-ring 16 at outlet 24 and is pulled out away from the body. Since the orthodontic O-ring 16 is flexible and deformable, it will easily deform so as to pass through outlet 14 past projections 27 (see FIG. 4b). In this manner, the dispensing tool touches only a single orthodontic O-ring, and the remaining orthodontic O-rings are not contaminated either by the hand of the user or by the ligation tool used to dispense and ligate the orthodontic O-ring. Thus, the aseptic quality of the undispensed O-rings is maintained. Thereafter, cover 33 may be placed around outlet 24 such that remaining orthodontic O-rings that may be safely stored for use at a later time.

It is to be understood that various modifications may be made to dispenser 10 without departing from the spirit of the scope of the present invention. FIGS. 5–14, illustrate various modified devices made in accordance with the present invention. These embodiments are similar to dispenser 10, like numerals indicating like parts.

In the preferred embodiment illustrated in FIGS. 1–3, the storage and delivery chamber 15 comprises three sections, a storage area 18, a funnel section 20, and a dispensing channel 22. Applicants believe that this type of configuration provides efficient and easy dispensing of the O-rings and minimizes the chances of O-rings potentially jamming in the storage chamber. However, the storage chamber 15 may take a variety of other configuration without departing from the scope of the present invention.

Figure 5:
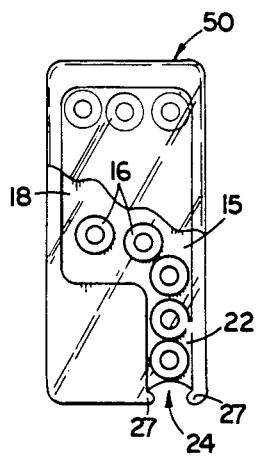
FIGS. 5–11 are top plan views of various modified embodiments of dispensers made in accordance with the present invention.

Referring to FIG. 5, there is illustrated a modified dispenser 50 made in accordance with the present invention. Dispenser 50 is similar to dispenser 10. However, in this embodiment, the funnel section 20 has been omitted. The storage area 18 directly communicates with dispensing channel 22.

Figure 6:
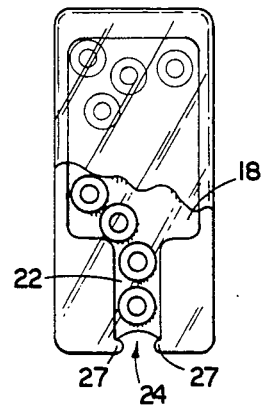

Referring to FIG. 6, in this embodiment the storage and delivery chamber 15 is similar to that of FIG. 5 except that the dispensing channel 22 is disposed approximately in the middle of the storage area 18.

Figure 7:
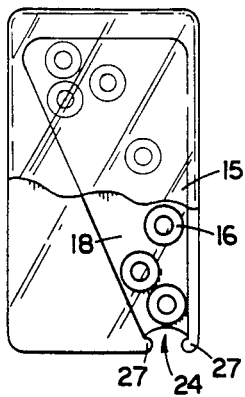

Referring to FIG. 7, there is illustrated yet another modified embodiment wherein the storage and delivery chamber 15 has a configuration which has a wide storage area 18 at one end which narrows down directly to outlet 24.

Figure 8:
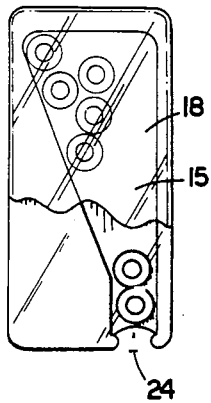

In FIG. 8, there is illustrated yet another modified embodiment similar to that of FIG. 5, except that in this embodiment a dispensing channel 22 is provided adjacent storage area 18.

Figure 9:
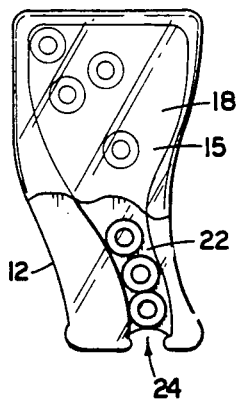

Referring to FIG. 9 there is illustrated yet another modified embodiment wherein the storage and delivery chamber 15 has a large storage area 18 at one end which quickly narrows down into dispensing channel 22. In this embodiment, the dispensing channel 22 and funnel section 18 are somewhat curved. Likewise, the body portion 12 is curved for easy manipulation.

Figure 10:
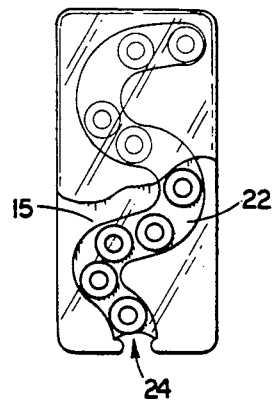

Referring to FIG. 10 there is illustrated yet another modified embodiment wherein the storage and delivery chamber 15 comprises a single serpentine-shape dispensing channel 22, wherein all the orthodontic O-rings 16 are placed in a row, one directly behind the other.

Figure 11:
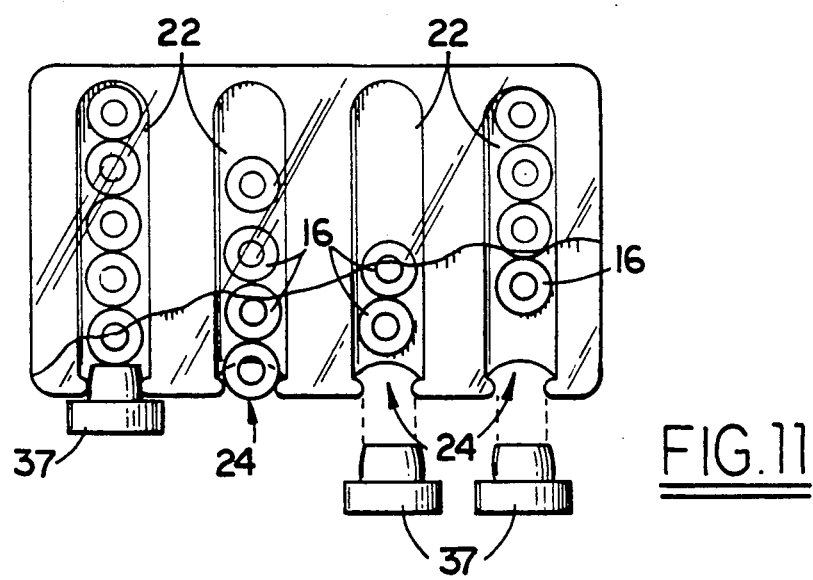

Referring to FIG. 11 there is illustrated yet another modified embodiment wherein a plurality of individual dispensing channels 22 are provided, each dispensing channel 22 having a plurality of orthodontic O-rings 16 disposed therein. A plug 37 for placement in each outlet 24 is provided so as to allow each dispensing channel 22 to be sealed from the environment until O-rings are to be dispensed.

Figure 12:
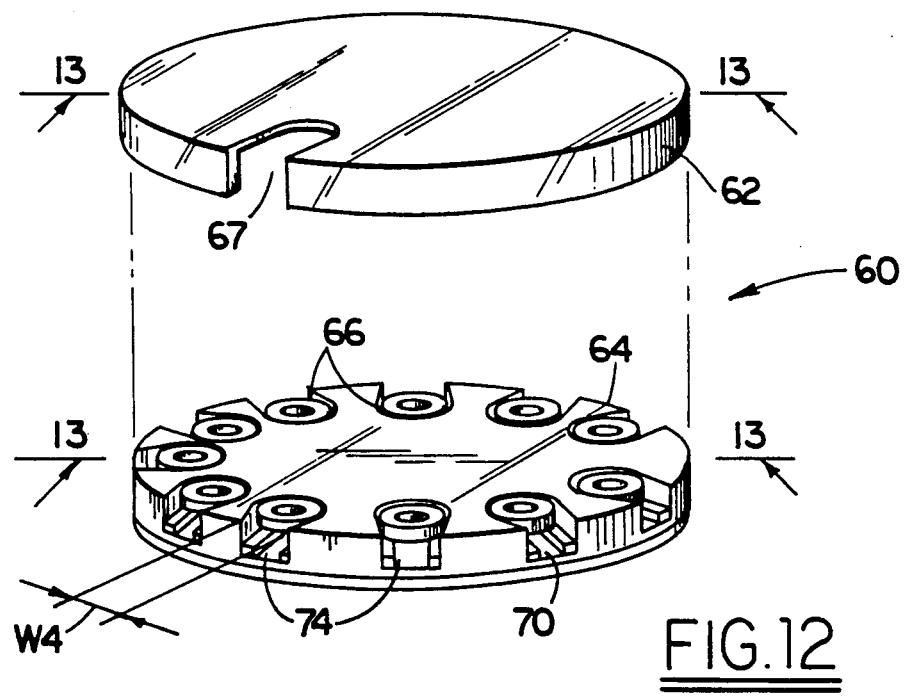
FIG. 12 is an exploded perspective view of an alternate dipensing device made in accordance with the present invention.
Figure 13:
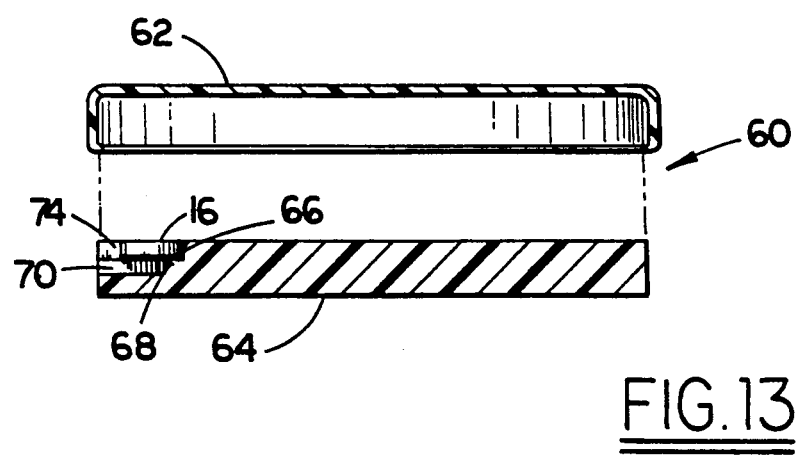
FIG. 13 is a cross sectional view taken along line XIII—XIII of FIG. 12.
Figure 14:
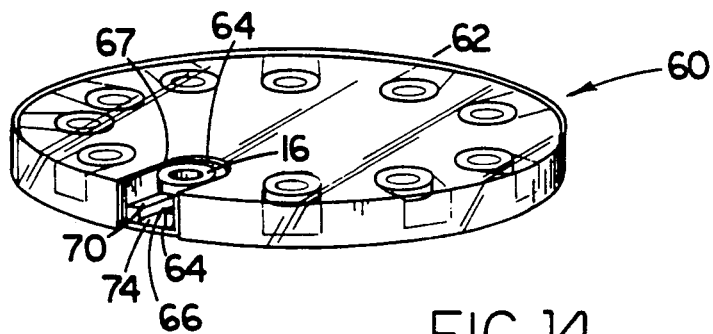
FIG. 14 is an assembled perspective view of the device illustrated in FIGS. 12 and 13.

Referring to FIGS. 12, 13 and 14, there is illustrated an exploded view of yet another modified embodiment made in accordance with the present invention. In this embodiment, dispenser 60 comprises cover 62 and a base portion 64 which snap together as illustrated in FIG. 14. In the preferred embodiment, the base portion 13 is substantially circular in shape and is provided with a plurality of individually spaced recesses 66, each capable of holding a single individual orthodontic O-ring 16. The base portion 64 can rotate within cover 62. Within each recesses 66 there is provided a shelf portion 68 for supporting O-ring 16. The recess 66 is shaped so as to allow the placement of a tool beneath said orthodontic O-ring. The cover 62 has a recess portion 67 for allowing access to the bottom side of an orthodontic O-ring within the recess 66. Each outlet 74 has a width W4 which is lightly less than the diameter D of orthodontic O-ring so as to restrict the O-ring from falling out of recess 66. The O-rings 16 are dispensed in the same manner as previously discussed with the embodiment illustrated in FIGS. 1–3. The cover is rotated to a position corresponding to one of the said orthodontic O-rings 16 and one of said recesses 66. An orthodontic tool is used to clasp the sides of the O-ring 16 and the O-ring 16 is simply pulled through the outlet 74. If the ligating tool is of the type that fits within the opening 30 of O-ring 16, then the tool is simply placed in the O-ring 16 and is pulled through outlet 74.

Figure 15:
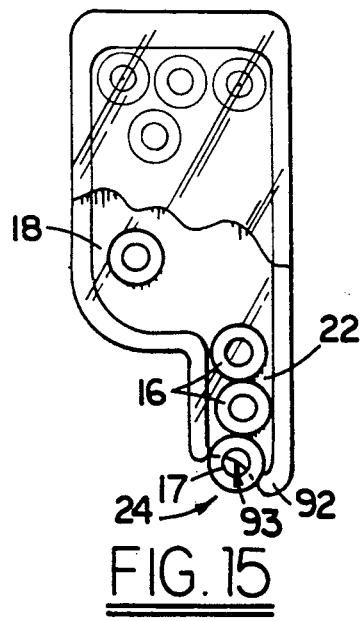
FIG. 15 is a top plan view of another embodiment of the present invention.
Figure 16:
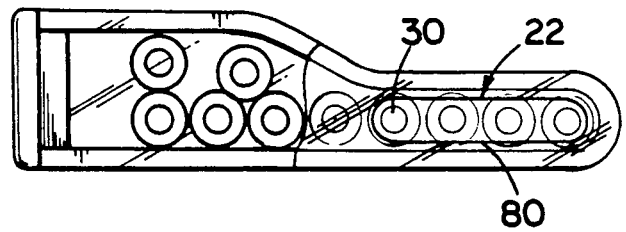
FIG. 16 is a top plan view of yet another embodiment of the present invention.

In the embodiments illustrated, the restricting of O-rings through the outlet is provided by a pair of projections adjacent the outlet 24 of the dispensing device. However, the present invention is not so limited. As illustrated in FIGS. 15 to 17, various other means may be used by which the O-ring 16 are restricted from exiting the outlet.

Referring to FIG. 16, a modified dispensing device is illustrated wherein an elongated slot 80 is provided at one end of dispensing channel 22. An O-ring 16 is dispensed by use of a ligating tool which is placed in the opening 30 of orthodontic O-ring 16. The tool is then opened so as to stretch (elongated) the O-ring 16 so that the O-ring may be simply pulled through the slot 80.

Referring to FIG. 15 there is illustrated a top plan view of another modified dispensing device made in accordance with the present invention illustrated the dispensing channel 22. The dispensing channel 22 is designed such that one wall of the dispensing channel 22 curves around in a curved portion 92 to reduce the width of the outlet 24 smaller than the diameter D of orthodontic O-ring 16. The outlet 24 is, as in the other embodiments, provided with a recess portion 93 which is similar in function to the recess portion 30 previously discussed.

Figure 17A:
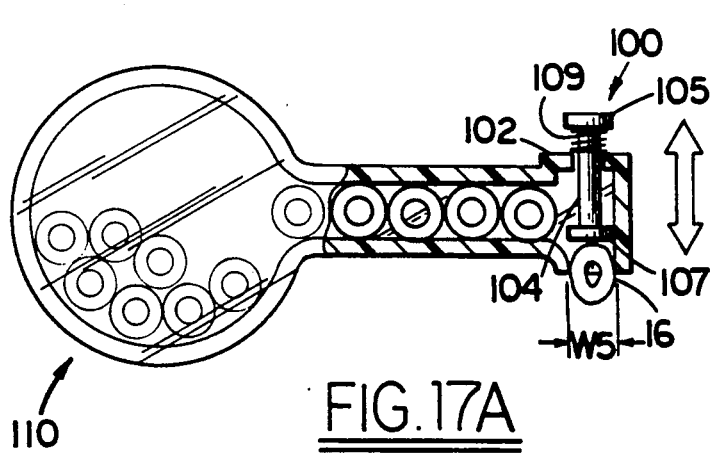
FIG. 17a is a top plan view of still another embodiment of the present invention.
Figure 17B:
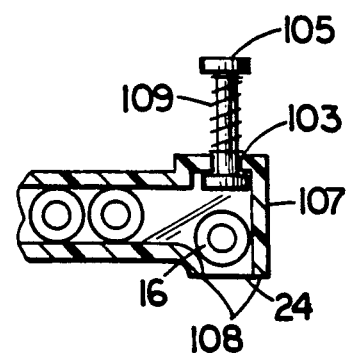
FIG. 17b is a fragmenting view of the device in FIG. 17a, illustrating the normal position of the plunger.

In FIGS. 17a and 17b, there is illustrated yet another modified device made in accordance with the present invention. In this particular embodiment, adjacent outlet 24 there is provided a plunger assembly 100 to assist in dispensing O-ring 16 onto outlet 24. Plunger assembly 100 comprises a plunger 102 which is biased so as to allow orthodontic O-ring 16 to freely flow to the end of dispensing channel 22. In the particular embodiment illustrated, the plunger 102 comprises an elongated cylindrical shaft 104 having a head 105 at one end and a head 107 at the other end. The shaft 104 passes through an opening 103 in the dispenser 110. The heads 105, 107 have a width so as to prevent the plunger 102 from passing opening 103. A spring 109 is placed around the cylindrical shaft 104 between the outer head 105 and outside surface of device 110 adjacent to opening 103. Spring 109 causes the plunger 102 to be biased as illustrated in FIGS. 17b. In order to dispense an orthodontic O-ring, the plunger 102 is pushed down as illustrated in FIG. 17a such that the O-ring is pushed between the side walls of outlet 24. The side walls 108 of outlet 24 are spaced a distance W5 apart which is less than the diameter D of orthodontic O-ring 16. The length L of plunger 102 is such that after being fully extended a portion of the orthodontic O-ring 16 is exposed past outlet 24 to allow it to be dispensed therefrom with a typical orthodontic ligating tool as previously discussed. Thus, O-ring 16 is preferably not exposed to the environment until plunger 102 pushes O-ring 16 in position to dispensing.

It is to be understood that various modifications may be made without departing from the scope of the present invention. For example, but not by way of limitation, the configuration and shape of the body portion of the dispenser may take a variety of shapes not illustrated. Additionally, the body as illustrated is comprised of two separate pieces, a base portion and cover, however, if so desired, the body may be made of a single mold injected piece whereby a plug is used to seal an access opening in the back of the body adjacent to the storage and delivery chamber after being filled with O-rings 16 and a second cap or plug may be used to cover the outlet. The scope of the present invention being defined in the following claims.

I claim:

1. A dispenser for dispensing orthodontic O-rings comprising:
a main body portion having a rigid storage and delivery chamber for holding and dispensing a plurality of separate O-rings made of an elastic material, said storage and delivery chamber having a substantially constant height which is slightly greater than the thickness of said orthodontic O-rings but less than twice the thickness of the O-rings such that said orthodontic O-rings would lie in a single plane, said storage and delivery chamber having a storage chamber, a funnel section adjacent one end of said storage chamber, a dispensing channel for aligning said O-rings in a single row disposed adjacent said funnel section for dispensing of said O-rings one at a time, a dispensing outlet disposed at the terminal end of said dispensing channel and means for restricting said O-rings from freely coming out of said outlet such that said O-rings must be deformed to allow dispensing from said outlet.

2. A dispenser according to claim 1 wherein said means for restricting said O-rings from freely coming out of said outlet comprise reducing the width of said outlet to a width slightly less than the outer diameter of said O-rings.

3. A dispenser according to claim 2 wherein at least one projection is provided for reducing the width of said outlet.

4. A dispenser according to claim 3 wherein two projections are provided for reducing the width of said outlet.

5. A dispenser according to claim 1 wherein said main body at said outlet is provided with a recess portion shaped to allow access to a portion of both sides of a O-ring for removal of said O-ring from said dispenser.

6. A dispenser according to claim 1 wherein said dispenser is further provided with means for sealing said outlet from the environment.

7. A dispenser according to claim 6 wherein said means for sealing said outlet comprises a cap that fits over the terminal portion of said dispensing section.

8. A dispenser according to claim 6 wherein said means for sealing said outlet comprises a plug that fits within said outlet.

9. A dispenser according to claim 1 wherein said main body portion comprises a base section and a top cover which are secured together.

10. A dispenser according to claim 9 wherein said main body portion is made of a transparent or translucent plastic material.

11. A dispenser for dispensing orthodontic O-rings comprising:

a main rigid body portion having at least one storage and delivery chamber for holding and dispensing at least one individual orthodontic O-ring made of an elastomeric material, said at least one storage and delivery chamber having a substantially constant height which is slightly greater than the thickness of an orthodontic O-ring but less than twice the thickness of the O-rings, said at least one storage and delivery chamber having an outlet for allowing dispensing of said O-ring one at a time, said main body further includes means for restricting said O-ring from freely coming out of said outlet such that said O-rings must be deformed to allow dispensing from said outlet.

12. A dispenser according to claim 11 wherein means for restricting said O-rings from freely coming out of said outlet comprise reducing the width of said outlet to a width slightly less than the outer diameter of said O-rings.

13. A dispenser according to claim 12 wherein at least one projection is provided for reducing the width of said outlet.

14. A dispenser according to claim 13 wherein two projections are provided for reducing the width of said outlet.

15. A dispenser according to claim 11 wherein said main body at said outlet is provided with a recess portion shaped to allow access to a portion of both sides of a O-ring for removal of said O-ring from said dispenser.

16. A dispenser according to claim 11 wherein said dispenser is further provided with means for sealing said outlet from the environment.

17. A dispenser according to claim 16 wherein said means for sealing said outlet comprises a cap that fits over the terminal portion of said dispensing section.

18. A dispenser according to claim 16 wherein said means for sealing said outlet comprises a plug that fits within said outlet.

19. A dispenser according to claim 11 wherein said main body portion comprises a base section and a top cover which are secured together.

20. A dispenser according to claim 19 wherein said main body portion is made of a transparent or translucent plastic material.

21. A dispenser according to claim 11 wherein said storage and delivery chambers comprise a dispensing channel for aligning said O-rings in a single row.

22. A dispenser according to claim 11 wherein said storage and delivery chamber comprises a storage chamber and dispensing channel, said outlet being located at the terminal end of said dispensing channel.

23. A dispenser according to claim 11 further comprising means for positioning said O-ring position for dispensing.

24. A dispenser according to claim 23 wherein said means for positioning said O-rings comprise a plunger assembly housing a biased plunger for moving O-rings in position for dispensing thereof by causing a portion of said O-ring to extend past said outlet to allow it to be removed by an appropriate tool.

* * * * *